US010280197B2

(12) United States Patent
Monikis et al.

(10) Patent No.: US 10,280,197 B2
(45) Date of Patent: May 7, 2019

(54) DISCOVERY OF THE FIRST SELECTIVE C5A RECEPTOR 2 (C5L2/C5AR2) LIGANDS

(71) Applicants: The Regents of the University of California, Oakland, CA (US); The Texas A & M University System, College Station, TX (US); The University of Queensland, St. Lucia (AU); University of Sheffield, Sheffield (GB)

(72) Inventors: Dimitrios Monikis, Riverside, CA (US); Christodoulos Floudas; Trent Woodruff, Carindale (AU); Matthew A. Cooper, Chapel Hill (AU); Daniel E. Croker, Kenmore (AU); Peter N. Monk, Sheffield (GB)

(73) Assignees: The Regents of the University of California, Oakland, CA (US); The Texas A & M University System, College Station, TX (US); The University of Queensland, St. Lucia (AU); The University of Sheffield, Sheffield (GB)

( * ) Notice: Subject to any disclaimer, the term of this patent is extended or adjusted under 35 U.S.C. 154(b) by 0 days.

(21) Appl. No.: 15/295,979

(22) Filed: Oct. 17, 2016

(65) Prior Publication Data
US 2017/0129921 A1 May 11, 2017

Related U.S. Application Data

(60) Provisional application No. 62/242,632, filed on Oct. 16, 2015.

(51) Int. Cl.
*A61K 38/00* (2006.01)
*C07K 5/00* (2006.01)
*C07K 7/06* (2006.01)
*C07K 5/087* (2006.01)
*C07K 5/083* (2006.01)

(52) U.S. Cl.
CPC .............. *C07K 7/06* (2013.01); *C07K 5/0808* (2013.01); *C07K 5/0812* (2013.01); *A61K 38/00* (2013.01)

(58) Field of Classification Search
CPC .... A61K 38/00; C07K 5/0808; C07K 5/0812; C07K 5/083; C07K 5/087; C07K 7/06
USPC .................................................. 530/300, 329
See application file for complete search history.

(56) References Cited

U.S. PATENT DOCUMENTS

2008/0148432 A1* 6/2008 Abad .................. C07K 14/415
800/279

OTHER PUBLICATIONS

Croker, D.E., et al, Discovery of functionally selective C5aR2 ligands: novel modulators of C5a signalling, Immunology and Cell Biology (2016) 94, 787-795.
Kemper, C., Targeting the Dark Horse of complement: the first generation of functionally selective C5aR2 ligands, Immunology and Cell Biology (2016), 1-2.
Klos A, Wende E, Wareham KJ, Monk PN. International Union of Pharmacology. LXXXVII. Complement Peptide C5a, C4a, and C3a Receptors. Pharmacological Reviews 2013; 65: 500-543.
Denny KJ, Coulthard LG, Jeanes A, Lisgo S, Simmons DG, Callaway LK et al. C5a receptor signaling prevents folate deficiency-induced neural tube defects in mice. J Immunol 2013; 190: 3493-9.
Monk PN, Scola AM, Madala P, Fairlie DP. Function, structure and therapeutic potential of complement C5a receptors. Br J Pharmacol 2007; 152: 429-448.
Manthey HD, Woodruff TM, Taylor SM, Monk PN. Complement component 5a (C5a). Int J Biochem Cell Biol 2009; 41: 2114-7.
Klos A, Tenner AJ, Johswich K-O, Ager RR, Reis ES, Kahl J. The role of the anaphylatoxins in health and disease. Mol Immunol 2009; 46: 2753-2766.
Woodruff TM, Ager RR, Tenner AJ, Noakes PG, Taylor SM. The role of the complement system and the activation fragment C5a in the central nervous system. Neuromolecular Med 2010; 12: 179-92.
Ward PA. The dark side of C5a in sepsis. Nature Rev Immunol 2004; 4: 133-142.
Riedemann NC, Guo R-F, Sarma VJ, Laudes IJ, Huber-Lang M, Warner RL et al. Expression and Function of the C5a Receptor in Rat Alveolar Epithelial Cells. J Immunol 2002; 168: 1919-1925.
Gerard NP, Gerard C. The chemotactic receptor for human C5a anaphylatoxin. Nature 1991; 349: 614-617.
Cain SA, Monk PN. The Orphan Receptor C5L2 Has High Affinity Binding Sites for Complement Fragments C5a and C5a des-Arg74. J Biol Chem 2002; 277: 7165-7169.
Okinaga S, Slattery D, Humbles A, Zsengeller Z, Morteau O, Kinrade MB et al. C5L2, a Nonsignaling C5A Binding Protein. Biochemistry 2003; 42: 9406-9415.
Van Lith LH, Oosterom J, Van Elsas A, Zaman GJ. C5a-stimulated recruitment of beta-arrestin2 to the nonsignaling 7-transmembrane decoy receptor C5L2. J Biomol Screen 2009: 14: 1067-75.
Bamberg CE, Mackay CR, Lee H, Zahra D, Jackson J, Lim YS et al. The C5a Receptor (C5aR) C5L2 is a Modulator of C5aR-mediated Signal Transduction. J Biol Chem 2010; 285: 7633-7644.

(Continued)

*Primary Examiner* — Julie Ha
(74) *Attorney, Agent, or Firm* — Brooks Kushman P.C.

(57) ABSTRACT

A method of selectively modulating the activity of C5a receptor 2 (C5aR2). The method includes exposing the receptor to a compound that selectively modulates C5aR2 compared to C5a receptor 1 (C5aR1). In some cases, the compound is peptide P32 or P59. Methods of recruiting β-arrestin 2 in a cell, modulating C5a-induced ERK1/2 activation in a macrophage, selectively inhibiting the release of IL-6 from a macrophage, are also provided.

12 Claims, 8 Drawing Sheets
Specification includes a Sequence Listing.

(56) References Cited

OTHER PUBLICATIONS

Scola AM, Johswich KO, Morgan BP, Klos A, Monk PN. The human complement fragment receptor, C5L2, is a recycling decoy receptor. Mol Immunol 2009; 46: 1149-62.

Chen N-J, Mirtsos C, Suh D, Lu Y-C, Lin W-J, McKerlie C et al, C5L2 is critical for the biological activities of the anaphylatoxins C5a and C3a. Nature 2007; 446: 203-207.

Gao H, Neff TA, Guo R-F, Speyer CL, Sarma JV, Tomlins S et al. Evidence for a functional role of the second C5a receptor C5L2. FASEB J 2005; 19: 1003-1005.

Croker DE, Halai R, Kaeslin G, Wende E, Fehlhaber B, Klos A et al. C5a2 can modulate ERK1/2 signaling in macrophages via heteromer formation with C5a1 and beta-arrestin recruitment. Immunol Cell Biol 2014; 92.631-639.

Jain U, Woodruff TM, Stadnyk AW. The C5a receptor antagonist PMX205 ameliorates experimentally induced colitis associated with increased IL-4 and IL-10. Br J Pharmacol 2013; 168: 488-501.

Huber-Lang M, Sarma VJ, Lu KT, McGuire SR, Padgaonkar VA, Guo R-F et al. Rote of C5a in Multiorgan Failure During Sepsis. J Immunol 2001; 156: 1193-1199.

Rittirsch D, Flierl MA, Nadeau BA, Day DE, Huber-Lang M, Mackay CR et al. Functional roles for C5a receptors in sepsis. Nat Med 2008; 14: 551-557. 1998; 115: 182-205.

Ward PA, Guo RF, Riedemann NC. Manipulation of the complement system for benefit in sepsis. Crit Care Res Pract 2012; 2012: 427607.

Fiocchi C. Inflammatory bowel disease: etiology and pathogenesis. Gastroenterology 1998; 115: 182-205.

Johswich K, Martin M, Bleich A, Kracht M, Dittrich-Breiholz O, Gessner JE et al. Role of the C5a receptor (C5aR) in acute and chronic dextran sulfate-induced models of Inflammatory bowel disease. Inflamm Bowel Dis 2009; 15: 1812-23.

Alloca M, Jovani M, Florino G, Schreiber S, Danese S. Anti-IL-8 Treatment for Inflammatory Bowel Diseases: Next Cytokine, Next Target. Curr Drug Targets 2013; 14: 1508-1521.

Riedemann NC, Neff TA, Guo RF, Bernacki KD, Laudes IJ, Sarma JV et al. Protective effects of IL-6 blockade in sepsis are linked to reduced C5a receptor expression. J Immunol 2003; 170: 503-7.

Li R, Coulthard LG, Wu MC, Taylor SM, Woodruff TM. C5L2: a controversial receptor of complement anaphylatoxin, C5a, FASEB J 2013; 27: 855-64.

Halai R, Bellows-Peterson ML, Branchett W, Smadbeck J, Kieslich CA, Croker DE et al. Derivation of ligands for the complement C3a receptor from the C-terminus of C5a. Eur J Pharmacol 2014; 745. 176-181.

Johswich K, Klos A. C5L2—an anti-inflammatory molecule or a receptor for acylation stimulating protein (C3a-desArg)? Adv Exp Med Biol 2007; 598: 159-80.

Johswich K, Martin M, Thalmann J, Rheinheimer C, Monk PN, Klos A. Ligand Specificity of the Anaphylatoxin C5L2 Receptor and Its Regulation on Myeloid and Epithelial Cell Lines. J Biol Chem 2006; 281: 39088-39095.

Kenakin T. Collateral efficacy in drug discovery: taking advantage of the good (allosteric) nature of 7TM receptors. Trends Pharmacol Sci 2007; 28: 407-415.

Croker DE, Halai R, Fairlie DP, Cooper MA. C5a, but not C5a-des Arg, induces upregulation of heteromer formation between complement C5a receptors C5aR and C5L2. Immunol Cell Biol 2013; 91: 625-633.

Bosmann M, Haggadone MD, Zetoune FS, Sarma JV, Ward PA. The interaction between C5a and both C5aR and C5L2 receptors is required for production of G-CSF during acute inflammation. Eur J Immunol 2013; 43: 1907-13.

Seow V, Lim J, Iyer A, Suen JY, Ariffin JK, Hohenhaus DM et al. Inflammatory responses induced by lipopolysaccharide are amplified in primary human monocytes but suppressed in macrophages by complement protein C5a. J Immunol 2013; 191: 4308-16.

Wang R, Lu B, Gerard C, Gerard NP. Disruption of the complement anaphylatoxin receptor C5L2 exacerbates inflammation in allergic contact dermatitis, J Immunol 2013; 191: 4001-9.

Hsu WC, Yang FC, Lin CH, Hsieh SL, Chen NJ. C5L2 is required for C5a-triggered receptor internalization and ERK signaling. Cell Signal 2014; 26: 1409-19.

Defea K. Beta-arrestins and heterotrimeric G-protein: collaborators and competitors in signal transduction. Br J Pharmacol 2008; 153 Suppl 1: S298-309.

Fan H, Bitto A, Zingarelli B, Luttrell LM, Borg K, Halushka PV et al. Beta-arrestin 2 negatively regulates sepsis-induced inflammation. Immunology 2010; 130: 344-51.

Riedemann NC, Guo R-F, Hollmann TJ, Gao H, Neff TA, Reuben JS et al. Regulatory role of C5a in LPS-induced IL-6 production by neutrophils during sepsis. FASEB J 2004; 18: 370-2.

Schorr CA, Dellinger RP. The Surviving Sepsis Campaign: past, present and future. Trends Mol Med 2014; 20: 192-4.

Scola AM, Higginbottom A, Partridge LJ, Reid RC, Woodruff T, Taylor SM et al. The role of the N-terminal domain of the complement fragment receptor C5L2 in ligand binding. J Biol Chem 2007; 282: 3664-71.

Reid RC, Yau MK, Singh R. Hamidon JK, Reed AN, Chu P et al. Downsizing a human inflammatory protein to a small molecule with equal potency and functionality. Nature Comrnun 2013; 4: 2802.

Bellows-Peterson ML, Fung HK, Floudas CA, Kieslich CA, Zhang L, Morikis D et al. De novo peptide design with C3a receptor agonist and antagonist activities: theoretical predictions and experimental validation. J Med Chem 2012; 55: 4159-68.

Klepeis JL, Floudas CA, Morikis D, Tsokos CG, Argyropoulos E. Spruce L et al. Integrated computational and experimental approach for lead optimization and design of compstatin variants with improved activity. J Am Chem Soc 2003; 125: 8422-3.

Verrack FAW. Human IL-23-producing type 1 macrophages promote but IL-10-producing type 2 macrophages subvert Immunity to (myco)bacteria. Proc Natl Acad Sci U S A 2004; 101: 4560-4565.

Halili MA, Andrews MR, Labzin LI, Schroder K, Matthias G, Cao C et al. Differential effects of selective HDAC inhibitors on macrophage inflammatory responses to the Toll-like receptor 4 agonist LPS. J Leukoc Biol 2010; 87: 1103-14.

Halai R, Croker DE, Suen JY, Fairlie DP, Cooper MA. A Comparative Study of Impedance versus Optical Label-Free Systems Relative to Labelled Assays in a Predominantly Gi Coupled GPCR (C5aR) Signalling. Biosensors 2012; 2: 273-290.

Bradford MM. A rapid and sensitive method for the quantitation of microgram quantities of protein utilizing the principle of protein-dye binding. Anal Biochem 1976; 72: 248-54.

Dutertre S, Croker D, Daly NL, Andersson A, Muttenthaler M, Lumsden NG et al. Conopressin-T from Conus tulipa reveals an antagonist switch in vasopressin-like peptides. J Biol Chem 2008; 283: 7100-8.

Kocan M, Dalrymple MB, Seeber RM, Feldman BJ, Pfleger KD. Enhanced BRET Technology for the Monitoring of Agonist-Induced and Agonist-Independent Interactions between GPCRs and beta-Arrestins. Front Endocrinol (Lausanne) 2010; 1: 12.

* cited by examiner

SEQUENCE LISTING

```
<160> NUMBER OF SEQ ID NOS: 3

<210> SEQ ID NO 1
<211> LENGTH: 7
<212> TYPE: PRT
<213> ORGANISM: Artificial Sequence
<220> FEATURE:
<223> OTHER INFORMATION: Peptide Ligand

<400> SEQUENCE: 1

Arg His Tyr Pro Tyr Trp Arg
1               5

<210> SEQ ID NO 2
<211> LENGTH: 6
<212> TYPE: PRT
<213> ORGANISM: Artificial Sequence
<220> FEATURE:
<223> OTHER INFORMATION: Peptide ligand

<400> SEQUENCE: 2

Leu Ile Arg Leu Trp Arg
1               5

<210> SEQ ID NO 3
<211> LENGTH: 8
<212> TYPE: PRT
<213> ORGANISM: Homo sapiens

<400> SEQUENCE: 3

His Lys Asp Met Gln Leu Gly Arg
1               5
```

DISCOVERY OF THE FIRST SELECTIVE C5A RECEPTOR 2 (C5L2/C5AR2) LIGANDS

CROSS-REFERENCE TO RELATED APPLICATIONS

This application claims the benefit of Provisional Patent Application No. 62/242,632, filed on Oct. 16, 2015, which is incorporated by reference herein.

STATEMENT REGARDING FEDERALLY SPONSORED RESEARCH OR DEVELOPMENT

This invention was made with Government support under Grant Nos. CTS-0426691 and CTS-0427103 from the National Science Foundation, and Grant Nos. 5R01GM052032 and R24 GM069736 from the National Institutes of Health. The Government has certain rights in this invention.

REFERENCE TO SEQUENCE LISTING

A Sequence Listing is submitted electronically via EFS-Web as an ASCII formatted text file with the name "1279605_SeqList"; the file was created on Oct. 17, 2016, is 0.9 kilobytes in size, and is incorporated herein by reference in its entirety.

BACKGROUND

Field of the Invention

The invention relates to the C5aR2 receptor and ligands thereof.

Related Art

The complement cascade is an ancient part of our innate immune system that can be activated following tissue injury/damage and in response to foreign bodies[1]. Following activation of the cascade the complement peptides C3a, C4a and C5a are generated prior to the termination of the cascade with the formation of the membrane attack complex[1]. C5a is a potent immunomodulator, but also has emerging roles outside of immunity during embryonic development[2]. Its production is tightly controlled in order to produce a rapid response to tissue injury/pathogens yet protect against unwanted activity on host tissue[1,3,4]. The disruption of this control can lead to the overproduction of C5a, which can lead to an uncontrolled inflammatory response. C5a has been associated with a number of autoimmune, inflammatory and neurodegenerative disorders[5,6] although, interestingly, the overproduction of C5a can lead to a down regulation of the immune response in some leukocytes, but have the opposite effect on other cell types[7,8].

Two receptors have been shown to bind C5a: the C5a receptor 1 (C5a1, CD88, or C5aR1) and the C5a receptor 2 (C5a2, C5L2, or C5aR2)[9,10]. C5a1 and C5a2 receptors are known to have important functions in many inflammatory conditions[3]. C5a1 is a classical G protein-coupled receptor (GPCR) and activation following C5a binding leads to predominantly $G\alpha_i$ activation which in turn activates multiple intracellular signalling pathways (including ERK, Akt, MAPK and PI3K) and β-arrestin recruitment for receptor desensitisation, recycling and perhaps also G-protein independent signalling[1,3]. C5a2 is a seven transmembrane domain receptor but is not coupled to G-proteins, partly due to key amino acid changes in the critical cytosolic DRY and NPXXY motifs where G-proteins have been shown to bind[11]. However, C5a2 has been shown to bind to β-arrestins[12,13]. C5a2 was originally thought to be a simple recycling decoy receptor, similar to the chemokine receptor D6[14]. This assumption is no longer accepted as C5a2 has now been shown to have both pro- and anti-inflammatory activities, and also to have its own functional role, which is likely to be regulated through β-arrestin recruitment and signalling[15,16]. We have recently published a model that potentially explains the contradictory role of C5a2 having both pro- and anti-inflammatory activities, through the modulation of C5a induced C5a1 signalling via C5aR2 mediated β-arrestin recruitment[17].

Two inflammatory conditions that are strongly associated with the dysregulation of C5a are sepsis and inflammatory bowel diseases (IBD)[7,18]. The detrimental effects of C5a in sepsis have been well studied and include paralysis of neutrophil immune function, promotion of septic cardiomyopathy, is a driver of apoptosis of adrenal medullar cells and thymocytes and consumptive coagulopathy which can all lead to multi-organ failure[5,19]. Using the caecal ligation and puncture (CLP) model of high grade sepsis in mice it was shown that C5a1 and C5a2 null animals had an 85% and 80% survival rate, respectively at day 3 compared to 0% in normal mice[20]. This data suggests that there is a cooperative interaction between C5a1 and C5a2 during the development of sepsis. Subsequently, this led to studies that showed that blocking of C5a or of both C5a receptors to be some of the most effective therapeutic treatment options for sepsis[21]. IBD is a chronic inflammatory condition of the gastrointestinal tract that is characterised by a relapsing/remitting inflammation caused by dysfunctioning mucosal T cells and irregular cytokine production that leads to damage to the mucosal lining of the intestine[22]. Studies using C5a1 knock-out mice have shown that C5a1 has detrimental effects in acute colitis induced by dextran sodium sulphate (DSS)[23], which suggested that, a C5a1 antagonist maybe an effective therapeutic option for IBD[18]. The pro-inflammatory cytokine IL-6 has been shown to play a key role in both of these conditions and is also involved in regulating the expression of C5a1 during sepsis[24,25].

SUMMARY

The physiological role of C5a2 under both pathological and normal conditions is still very controversial, but it is apparent that it has an important role in C5a biology[26]. A major issue for the field has been the unavailability of selective ligands for C5a2, as current ligands either target C5a1 alone or interact with both receptors. Recently, the inventors have discovered selective C3aR partial agonists from a library of small peptides designed to target C5a1, giving evidence for the promiscuity of ligands designed to target the complement activation peptide receptors[27]. As described herein, the same library of small peptides is investigated for activity at C5a2, first using a radioligand binding assay to C5a2 expressing membranes, followed by a bioluminescence resonance energy transfer (BRET) based β-arrestin 2 recruitment assay. Further investigated was whether the C5a2 ligands could modulate human monocyte derived macrophages (HMDMs) functions including cytokine release and ERK1/2 activation. Described herein are the first selective C5a2 ligands, which can recruit β-arrestin 2, modulate C5a-induced ERK1/2 activation and selectively inhibit the release of IL-6 from macrophages.

In one aspect, a method of selectively modulating the activity of C5a receptor 2 (C5aR2) is provided. The method includes exposing the receptor to a C5aR2 ligand that selectively modulates C5aR2 compared to C5a receptor 1

(C5aR1). In the method: a) the C5aR2 can be on the surface of or inside a cell; b) the cell can be in a subject or in culture; c) the ligand can act as a C5aR2 agonist or antagonist; or d) any combination of a)-c). Examples of cells expressing C5aR2 on their surface include cells of myeloid origin (e.g., monocyte, macrophage or neutrophil), as well as lymphocytes, and many non-immune cells including endothelial cells, adipocytes, and cells within the central nervous system including neurons, astrocytes and glial cells.

In another aspect, a method of recruiting β-arrestin 2 in a cell, modulating C5a-induced ERK1/2 activation in a macrophage, selectively inhibiting the release of IL-6 from a macrophage, or any combination thereof, is provided. The method includes exposing the cell or macrophage to a C5aR2 ligand that selectively modulates C5aR2 compared to C5aR1. In the method, the cell or macrophage can be in culture or in a subject. The cell can be, but is not limited to, a cell of myeloid origin (e.g., monocyte, macrophage or neutrophil), as well as lymphocytes, and many non-immune cells including endothelial cells, adipocytes, and cells within the central nervous system.

In a further aspect, a method of treating a disease involving C5aR2 in a subject in need thereof is provided. The method includes exposing the subject to a C5aR2 ligand that selectively modulates C5aR2 compared to C5aR1. In the method, the disease can be sepsis, IBD, other inflammatory diseases such as rheumatoid and osteoarthritis, reperfusion injuries including myocardial and cerebral infarction, transplantation injuries, and neuroinflammatory/degenerative conditions including, but not limited to, Parkinson's, Alzheimer's, Huntington's and motor neuron disease such as, but not limited to, amyotrophic lateral sclerosis.

In any of the methods described above involving selective modulation of C5aR2 compared to C5aR1: a) the ligand can be a polypeptide or peptide that includes the amino acid sequence RHYPYWR (SEQ ID NO:1) or the amino acid sequence LIRLWR (SEQ ID NO:2); b) the ligand can be a peptide (such as peptide P32 or peptide P59) that includes SEQ ID NO:1 or SEQ ID NO:2, or can be an analog, sequence variant, peptide surrogate, or peptidomimetic of the peptide; in some embodiments, the ligand includes amino acid sequence TyrTrpArg of SEQ ID NO:1 or LeuTrpArg of SEQ ID NO:2; c) the subject can be a human or other mammal. In some embodiments, the receptor, cell or subject can be exposed to two or more compounds that selectively modulate C5aR2 compared to C5aR1. For example, the receptor, cell or subject can be exposed to both peptide P32 and peptide P59.

In another aspect, a C5aR2 ligand that selectively modulates C5aR2 compared to C5aR1 is provided. The ligand: a) can be a C5aR2-modulating ligand used in any one of the methods described above; b) can be a polypeptide or peptide that includes SEQ ID NO:1 or SEQ ID NO:2; c) can be a peptide (such as peptide P32 or peptide P59) that includes SEQ ID NO:1 or SEQ ID NO:2, or can be an analog, sequence variant, peptide surrogate, or peptidomimetic of the peptide; and in some embodiments, the ligand includes amino acid sequence TyrTrpArg of SEQ ID NO:1 or LeuTrpArg of SEQ ID NO:2.

BRIEF DESCRIPTION OF THE DRAWINGS

For a more complete understanding of the present invention, reference is now made to the following descriptions taken in conjunction with the accompanying drawings, in which.

DETAILED DESCRIPTION

In various aspects, selective C5aR2 ligands that selectively modulate C5aR2 compared to C5aR1 are provided. In some embodiments, the ligand can be a polypeptide or peptide that comprises SEQ ID NO:1 or SEQ ID NO:2. In general, a polypeptide contains about 100 or more amino acids, and a peptide contains from 2 to about 100 amino acids.

In some embodiments, amino acid sequence variants of a polypeptide or peptide are provided. An amino acid sequence variant can be a substitutional, insertional or deletion variant. Deletion variants lack one or more residues of the native or starting polypeptide or peptide that are not essential for function activity, for example. Insertional mutants typically involve the addition of material at a non-terminal point in the polypeptide. This may include the insertion of a functional motif or simply a single residue.

Substitutional variants typically contain the exchange of one amino acid for another at one or more sites within the polypeptide or peptide, and may be designed to modulate one or more properties of the polypeptide or peptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Sequence variants can have about 70% or more, about 80% or more; about 85% or more, about 90% or more, about 95% or more, or about 99% or more, sequence similarity to a starting polypeptide or peptide. A sequence comparison can be performed, for example, using Clustal Omega, MUSCLE, MView, or MAFFT sequence comparison programs. In comparing sequences, a segment of comparison between one polypeptide, or peptide, and another may be about 100% of the amino acids of the length being compared, or about 95%, about 85%, or about 80% of the amino acids of the length being compared.

An analog of a peptide can be a peptide which has been modified but retains the ability to modulate C5aR2. Modification can be by, for example, truncation, substitution, covalent attachment to another moiety, and the like. Peptide analogs include, for example, esters, amides, prodrugs, and salt forms of peptides. Peptide analogs can include peptides that have been covalently modified by attachment to another moiety, such as for example a lipophilic moiety (e.g. a fatty acid), a carrier molecule, or a heterologous polypeptide to produce a fusion protein. In certain embodiments, an analog can contain conservative substitutions as described above.

A peptidomimetic is a peptide-like molecule that comprises the same general structure of a corresponding polypeptide or peptide, but which includes modifications that increase its stability or biological function. For example, a peptidomimetic can be a chemically modified peptide; or a "reverso" analogue of a given peptide, which means that the peptidomimetic comprises the reverse sequence of the peptide; or comprise one or more amino acids in a "D" configuration (e.g., D-amino acids), providing an "inverso" analogue; or contain non-naturally occurring amino acids; or a combination thereof. A peptidomimetic can also include a peptoid, wherein the side chain of each amino acid is appended to the nitrogen atom of the amino acid as opposed to the alpha carbon. Other examples can be found, for example, in Goodman and Ro, Peptidomimetics for Drug Design, in "Burger's Medicinal Chemistry and Drug Discovery" Vol. 1 (ed. M. E. Wolff; John Wiley & Sons 1995).

A peptide surrogate refers to a compound that can be used structurally and/or functionally in place of a target peptide.

In embodiments involving a subject, the subject can be a human or other mammal. Examples of mammals include, but are not limited to, dogs, cats, rats, mice, monkeys, apes, cows, sheep, pigs, and rabbits.

Similarly, in embodiments involving cells, the cells can be from a human or other mammal, such as, but are not limited to, dog, cat, rat, mouse, monkey, ape, cow, sheep, pig, and rabbit.

Standard methods for producing and making peptides, polypeptides and nucleic acids can be applied, if applicable. Standard recombinant methods can be developed, including design of recombinant nucleic acids encoding constructs. See, e.g., Thompson D. A. Cell and Molecular Biology Manual 2011. Expression vectors, e.g., with promoters operably linked to coding regions, can be devised. Cells comprising the vectors are provided, including recombinant prokaryote cells and recombinant eukaryote cells such as recombinant yeast and recombinant mammalian cells. Compatible expression methodologies can also be developed.

Some embodiments include a pharmaceutical composition. Although oral administration of a compound is a preferred route of administration, other means of administration such as nasal, topical or rectal administration, or by injection or inhalation, are also contemplated. Depending on the intended mode of administration, the pharmaceutical compositions may be in the form of solid, semi-solid or liquid dosage forms, such as, for example, tablets, suppositories, pills, capsules, powders, liquids, suspensions, ointments or lotions, preferably in unit dosage form suitable for single administration of a precise dosage. The compositions can include an effective amount of the selected compound in combination with a pharmaceutically acceptable carrier and, in addition, may include other pharmaceutical agents such as anti-viral agents, adjuvants, diluents, buffers, and the like. The compounds may thus be administered in dosage formulations containing conventional non-toxic pharmaceutically acceptable carriers, adjuvants and vehicles. One skilled in this art may formulate the compound in an appropriate manner, and in accordance with accepted practices, such as those disclosed in Remington's Pharmaceutical Sciences, Gennaro, Ed., Mack Publishing Co., Easton, Pa. 1990. The amount of active compound administered will be dependent on the subject being treated, the subject's weight, the manner of administration and the judgment of the prescribing physician.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan mono-laurate, triethanolamine sodium acetate, triethanolamine oleate, etc. Actual methods of preparing such dosage forms are known, or will be apparent, to those skilled in this art. For oral administration, the composition will generally take the form of a tablet or capsule, or may be an aqueous or nonaqueous solution, suspension or syrup. Tablets and capsules for oral use will generally include one or more commonly used carriers such as lactose and corn starch. Lubricating agents, such as magnesium stearate, are also typically added. When liquid suspensions are used, the active agent may be combined with emulsifying and suspending agents. If desired, flavoring, coloring and/or sweetening agents may be added as well. Other optional components for incorporation into an oral formulation herein include, but are not limited to, preservatives, suspending agents, thickening agents, and the like.

The present invention may be better understood by referring to the accompanying examples, which are intended for illustration purposes only and should not in any sense be construed as limiting the scope of the invention.

EXAMPLE 1

The complement cascade is comprised of a highly sophisticated network of innate immune proteins that are activated in response to invading pathogens or tissue injury. The complement activation peptide, C5a, binds two seven transmembrane receptors; namely the C5a receptor 1 (C5a1/C5aR1) and C5a receptor 2 (C5a2/C5L2/C5aR2). C5a2 is a non-G-protein-signalling receptor whose biological role remains controversial. Some of this controversy arises due to the lack of selective ligands for C5a2. A small peptide library of 61 ligands based on the C-terminus of C5a was tested for the ability to selectively activate C5a2 using direct C5a2 binding, β-arrestin 2 recruitment assays and measuring cytokine release and ERK1/2 activation in human monocyte derived macrophages (HMDMs). From the 61 ligands tested, two (referred to herein as P32 and P59) exhibited dose dependent inhibition of $^{125}$I-C5a binding to C5a2. Both peptides could also recruit β-arrestin 2 via C5a2, but not to the same extent as C5a with no effect on β-arrestin 2 recruitment via C5a1. P32 and P59 could selectively inhibit the release of IL-6 from LPS co-stimulated HMDMs through C5a2, as the inhibition of IL-6 release was maintained in the presence of the C5a1 antagonist PMX53. Finally, P32 and P59 had no direct effect on ERK1/2 activation but could partially inhibit C5a-induced ERK1/2 activation in HMDMs. Here is reported the first functionally selective ligands for C5a2 with novel pharmacology that can selectively modulate C5a1 induced ERK1/2 activation and IL-6 release from macrophages.

Results
Binding of Complement Proteins to C5a2

Figure 1:
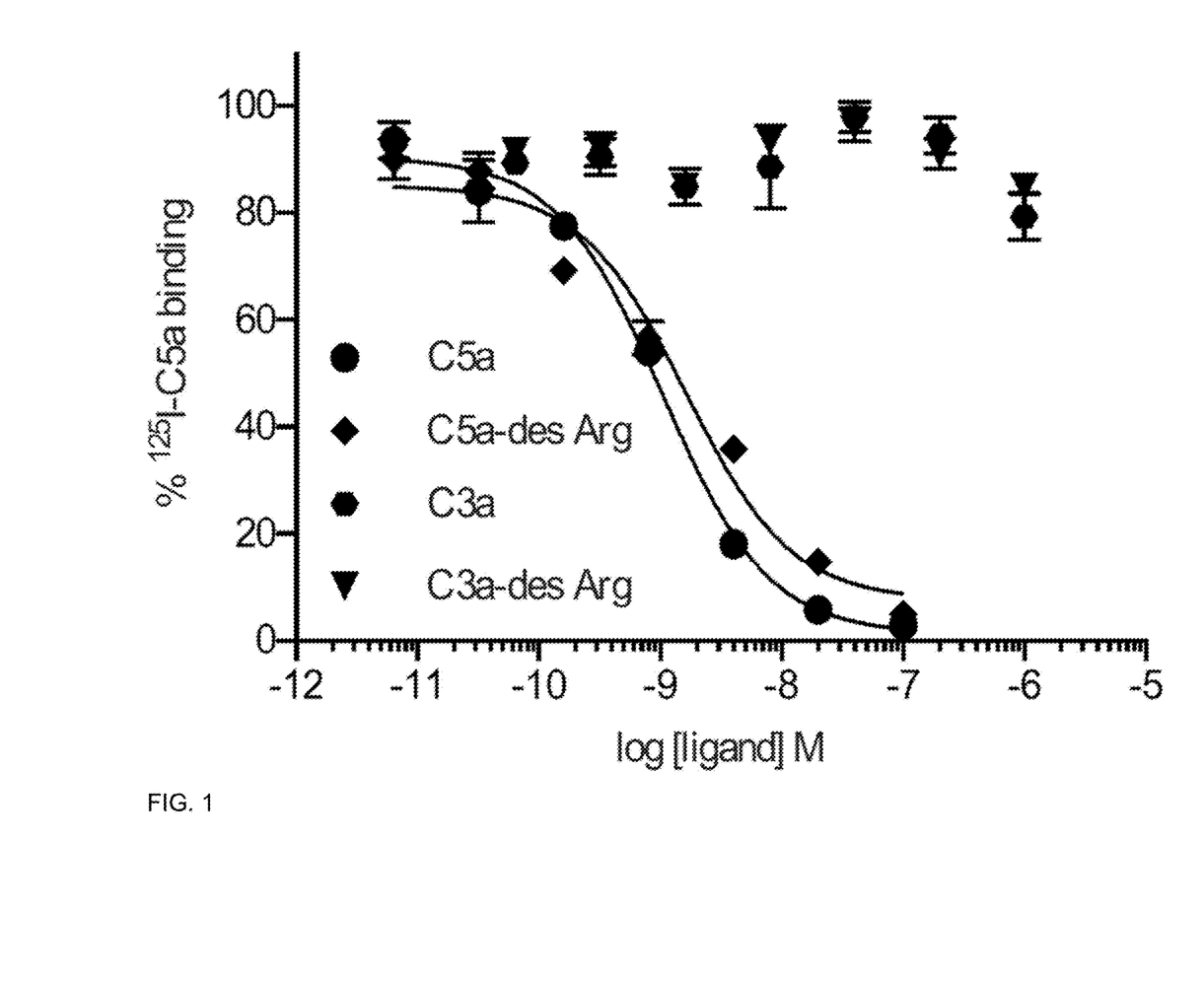
FIG. 1 is a graph showing C5a2 binding affinity for the complement proteins C3a, C3a-des Arg, C5a and C5a-des Arg. Binding affinities for complement proteins: C5a $K_i=1.3\pm0.3$ nM, C5a-des Arg $K_i=1.5\pm0.4$ nM, C3a and C3a-des Arg $K_i>1$ μM. Data is representative of at least three independent experiments performed in triplicate (n=3-5). Data is normalised to C5a response for each experiment. Error bars represent SEM.

There is still some controversy in the literature as to whether C5a2 is the receptor for C3a-des Arg/acylation-stimulating protein (ASP), with more recent data in the literature that suggests this is not the case[28]. To further address this issue, C5a2 SPA was used to test for the binding of C3a or C3a-des arg to C5a2. In these studies, neither C3a nor C3a-des Arg (at concentrations up to 1 μM) showed any discernible displacement of $^{125}$I-C5a from Flp-In CHO-C5a2 membrane preparations, whilst both C5a and C5a-des Arg show full inhibition (FIG. 1). This confirms that C3a and C3a-des Arg (ASP) do not bind to human C5a2 as has been previously reported[29].

Screening Peptide Library for Binding to C5a2

Figure 2:
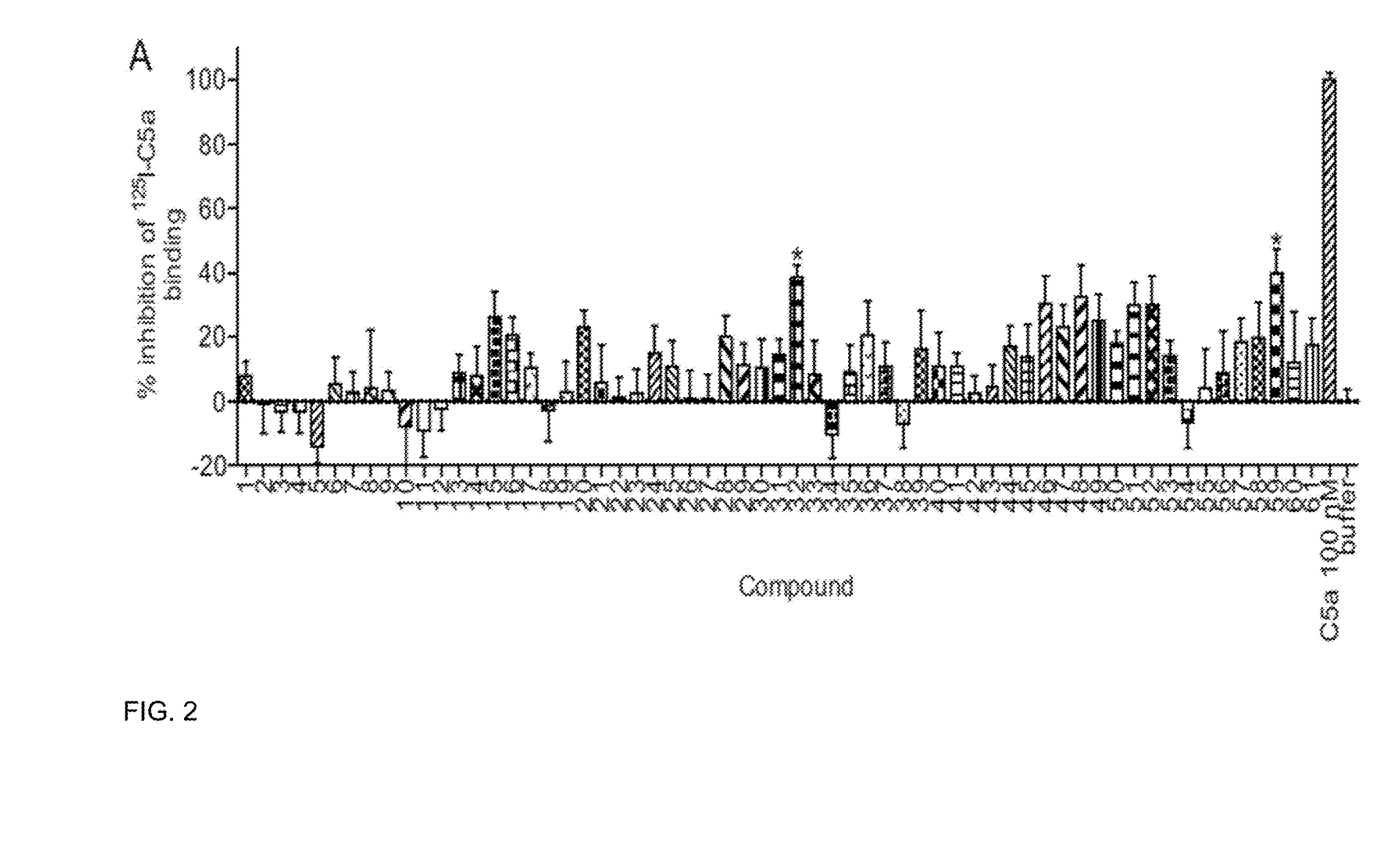
FIG. 2 is a panel showing the identification and verification of hits at C5a2 from 61-peptide library. (2A) Testing of 61-peptide library at 100 μM for inhibition of $^{125}$I-C5a binding to C5a2 membranes. Asterisk indicate hits that show significant inhibition of $^{125}$I-C5a binding compared to buffer control, P<0.05. (2B) Sigmoidal dose-response curves for the hits P32, P59 and control compound P48 for inhibition of $^{125}$I-C5a binding to C5a2 membranes. Data are representative of at least three independent experiments performed in triplicate (n=3-4). Data is normalised to C5a response for each experiment. Error bars represent SEM. *P<0.05 by one-way ANOVA followed by Dunnett's post hoc test.

Initially the library was screened at a single concentration of 100 μM for inhibition of $^{125}$I-C5a binding to C5a2 membranes. Of the 61 peptides only two peptides (P32 and P59) showed significant inhibition (P<0.05) of $^{125}$I-C5a binding to C5a2 membranes when compared to buffer control (FIG. 2A). P32, P59 and P48 (tested as negative control compound, due to P48 also showing inhibition of $^{125}$I-C5a binding) were than screened using a full concentration response up to a maximum concentration of 500 μM (maximum concentration achievable due to level of DMSO in assay). Both P32 and P59 dose-dependently inhibited $^{125}$I-C5a binding to C5aR2 and C5aR1 membranes with $K_i$ in the μM range, whereas P48 only inhibited $^{125}$I-C5a binding to C5aR1 (Table 1 and FIG. 2B). P32 had a similar affinity for both C5aR2 (223 μM) and C5aR1 (234 μM), whereas P59 had ~10-fold higher affinity for C5aR2 (48 μM) over C5aR1 (466 μM). P32 and P59 were previously shown to have no activity (either as an agonist or antagonist) up to a concentration of 100 μM, when the library was previously screened for activity at C3aR and C5a1[27].

TABLE 1

Binding affinity and efficacy for ligands at C5a2

| | Sequence | C5a2 binding $K_i$ ± SD | C5a2-β-arrestin 2 BRET $EC_{50}$ ± SD | Recruitment (% of C5a) |
|---|---|---|---|---|
| C5a | | 1.3 ± 0.3 nM | 50.3 ± 4.2 nM | 100 |
| P32 | Ac-RHYPYWR | 223 ± 180 μM | 5.9 ± 3.4 μM | 28.8 |
| P59 | Ac-LIRLWR | 48 ± 35 μM | 7.6 ± 0.6 μM | 52.9 |

P32 and P59 Recruit β-arrestin 2 Via C5a2, but not C5a1, and are Unable to Up-regulate Heteromer Formation between C5a1 and C5a2

Figure 3:
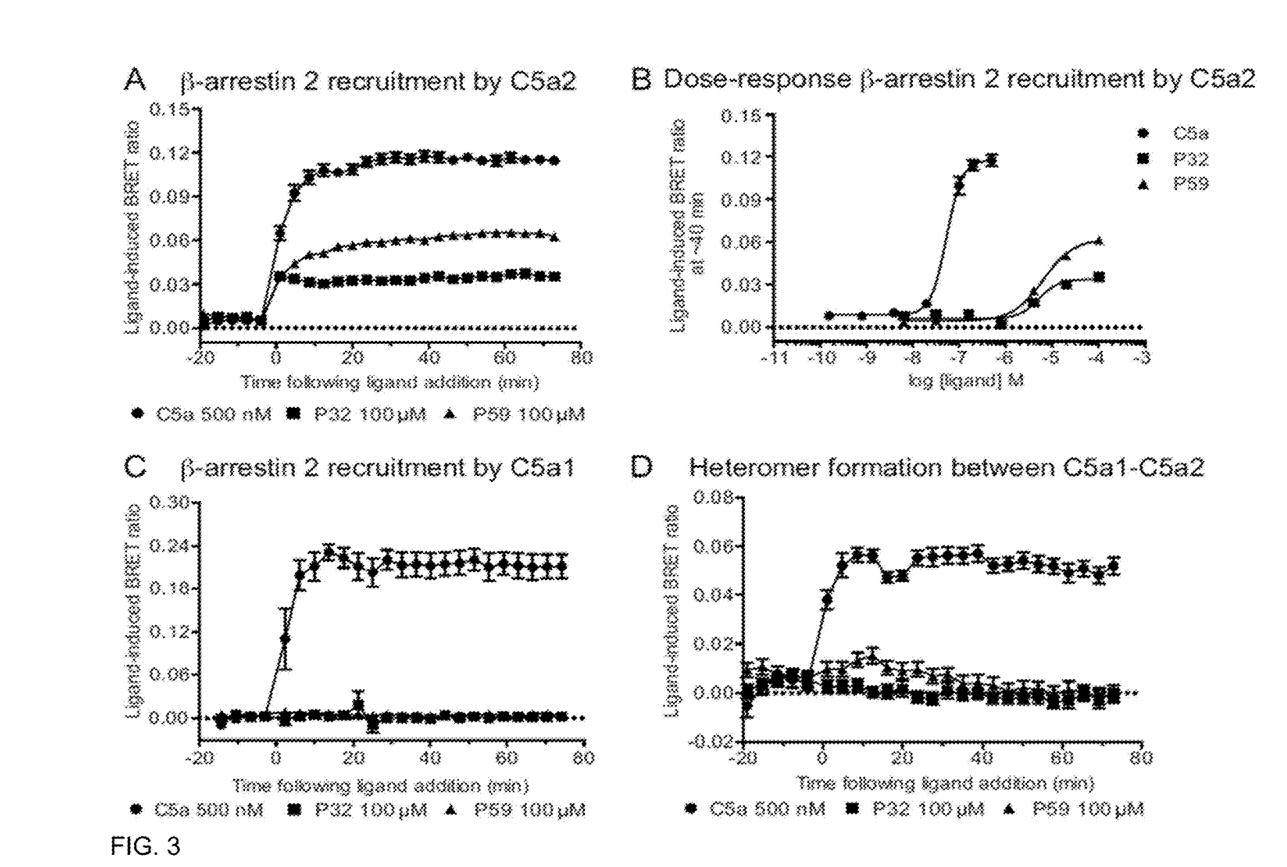
FIG. 3 is a panel of graphs showing BRET assay testing hits for β-arrestin 2 recruitment by C5a1 or C5a2 and ligand induced heteromer formation between C5a receptors. (3A) Ligand-induced BRET ratio for β-arrestin 2 recruitment by C5a2 for C5a (500 nM), P32 or P59 (100 μM). (3B) Sigmoidal dose response curves for C5a, P32 or P59 for β-arrestin 2 recruitment by C5a2 calculated at ~40 min after ligand addition. (3C) Ligand-induced BRET ratio for β-arrestin 2 recruitment by C5a1 for C5a (500 nM), P32 or P59 (100 μM). (3D) Ligand-induced BRET ratio for up-regulation of heteromer formation between C5a1-C5a2 for C5a (500 nM), P32 or P59 (100 μM). Data are representative of at least three independent experiments performed in triplicate (n=3-4). Error bars represent SEM.

Due to the non G-protein signalling nature of C5a2, a BRET C5a2-β-arrestin 2 recruitment assay, previously developed in the inventors lab[17], was used to test peptides for functional activity at C5a2. Both, P32 and P59 were identified as partial agonists for the recruitment of β-arrestin 2 via C5a2 (Table 1). Neither ligand could recruit β-arrestin 2 to the same level as C5a, but they could recruit β-arrestin 2 at a similar rate to C5a (FIG. 3A). P32 and P59 dose dependently recruited β-arrestin 2 via C5a2 with significantly higher efficacy than their binding affinity for C5a2 (FIG. 3B, Table 1), in contrast to the reduced potency exhibited by C5a. It is now accepted that GPCRs act as prototypic allosteric proteins that don't necessarily have a one to one relationship between ligand affinity and efficacy with interacting intracellular partners[30]. Neither, P32 or P59 could recruit β-arrestin 2 via C5a1 (FIG. 3C), giving further evidence for the selectivity of the ligands for C5a2. In addition, the complete library was tested for ligand induced β-arrestin 2 recruitment at C5a1 and C5a2 using DiscoverX PathHunter kits. Only P32 and P59 showed activity at C5a2 and no peptide had any activity at C5a1 (data not shown). The inventors have previously shown that high concentrations of C5a can up-regulate heteromer formation between C5a1-05a2[31], but neither P32 or P59 were able to up-regulate heteromer formation between the C5a receptors (FIG. 3D).

P32 and P59 Inhibit IL-6 Release from HMDM

Figure 4:
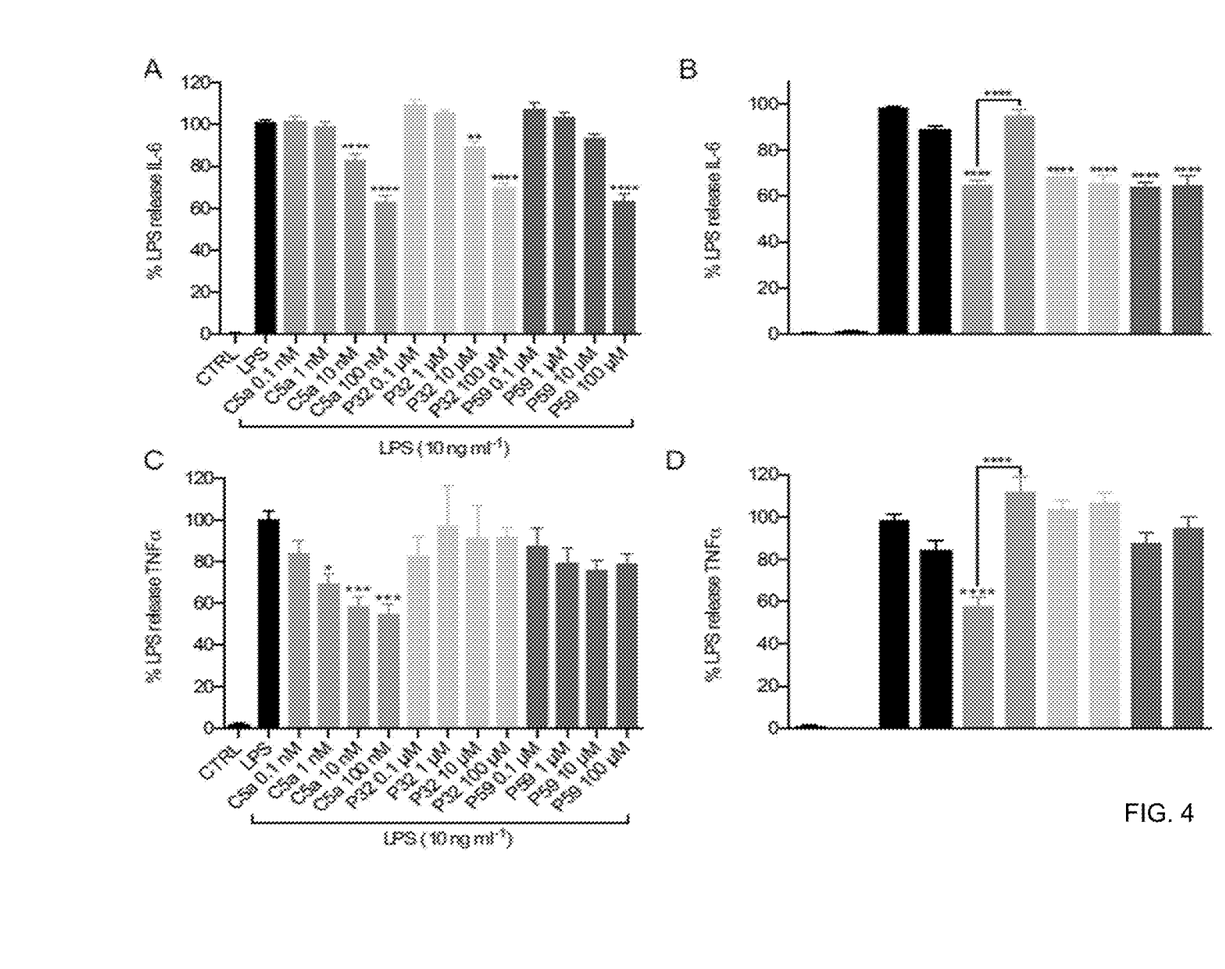
FIG. 4 is a panel of graphs showing the testing P32 and P59 for effects on cytokine release from LPS stimulated HMDM. Measurement of human inflammatory cytokines IL-6 (4A, 4B), TNFα (4C, 4D) and IL-10 (4E, 4F) release from HMDM, 24 h after co-stimulation with LPS (10 ngml$^{-1}$) and C5a (0.1-100 nM), P32 or P59 (0.1-100 μM) with or without C5a1 antagonist PMX53 (10 μM) present. Cytokine release was quantified by ELISA. Data is representative of five independent HMDM donors performed in triplicate (n=5). CTRL represents non-stimulated HMDM. Data is normalised to LPS response (100%) for each donor. Error bars represent SEM. *P<0.05,  P<0.01, * P<0.001, **** P<0.0001 by one-way ANOVA followed by Dunnett's post hoc test or Sidak's post hoc test for comparisons+/−PMX53.

The active C5a2 hits were tested for the ability to modulate LPS induced cytokine release from HMDM. It has been shown that C5a receptors are important modulators of LPS stimulated cytokine release from macrophages[32]. C5a dose-dependently inhibits the release of the pro-inflammatory cytokines IL-6 and TNFα, whilst increasing the release of the anti-inflammatory cytokine IL-10 from LPS stimulated HMDMs[33]. In the study described herein, P32 and P59 were shown to significantly inhibit the release of IL-6, but had no effect on TNFα and IL-10 from LPS stimulated HMDMs (FIG. 4). P32 showed significant inhibition of IL-6 release at two (10 and 100 µM) of the four doses tested (0.1-100 µM) (FIG. 4A) whereas P59 only showed significant inhibition of IL-6 at 100 µM, the highest dose tested. Interestingly, both P32 and P59 at 100 µm had a similar maximum level of inhibition of IL-6 as C5a. To further prove that P32 and P59 are acting via C5a2, LPS stimulated cytokine release from HMDM was quantified in the presence of the C5a1 antagonist, PMX53 (FIG. 4B, D, F). In the presence of PMX53 the effects of C5a on IL-6, TNFα and IL-10 are completely blocked, whereas P32 and P59 inhibition of IL-6 release is unaffected. This result gives further evidence for the functional selectivity of P32 and P59 for C5a2. This data suggests that a significant portion of the IL-6 inhibition can be modulated via specific activity at C5a2.

P32 and P59 Inhibit C5a-induced ERK1/2 Activation in HMDM

Figure 5:
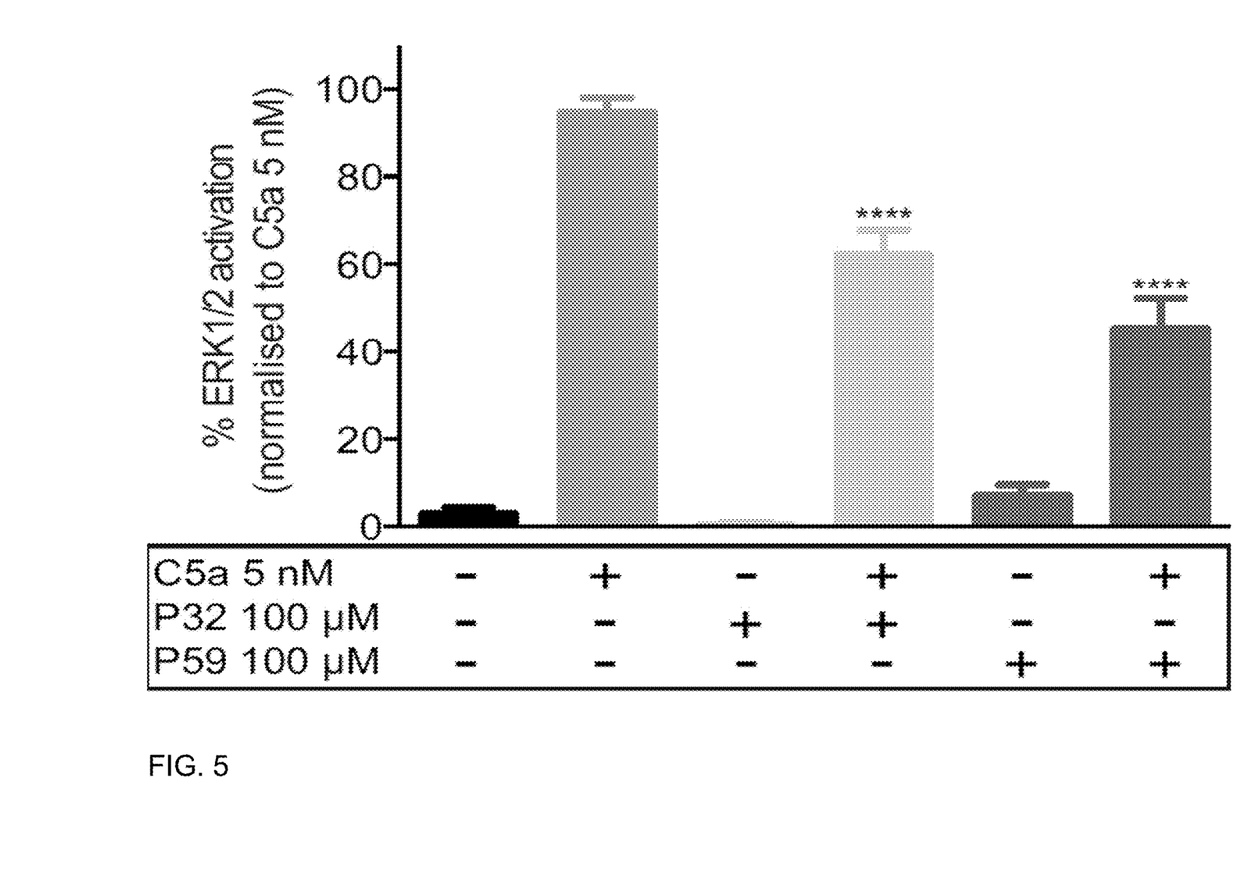
FIG. 5 is a graph showing that P32 and P59 inhibit C5a-induced ERK1/2 activation in HMDM. pERK quantified by Surefire ERK1/2 kit. Data is normalised to C5a 5 nM (100%) for each donor. Data are representative of at least three independent experiments HMDM donors performed in triplicate (n=3-5). Error bars represent SEM. **** P<0.0001 by one-way ANOVA followed by Dunnett's post hoc test.

It is well known that C5a binding to C5a1 induces rapid and robust ERK1/2 activation; the inventors have recently shown that C5a binding to C5a2 has no such effect on ERK1/2 activation[17]. Though C5a2 has been shown to modulate C5a1 ERK1/2 activation, this has only been tested using C5a2 antibodies[13, 17]. P32 and P59 were tested for their ability to either directly stimulate ERK1/2 activation or inhibit C5a-induced ERK1/2 activation by C5a1 in HMDM (FIG. 5). Neither P32 or P59 could induce ERK1/2 activation alone but both could significantly inhibit C5a-induced ERK1/2 activation in HMDM. This data supports the theory that C5a2 can modulate C5a1 induced ERK1/2 activation most likely through a β-arrestin dependent mechanism.

Figure 6:
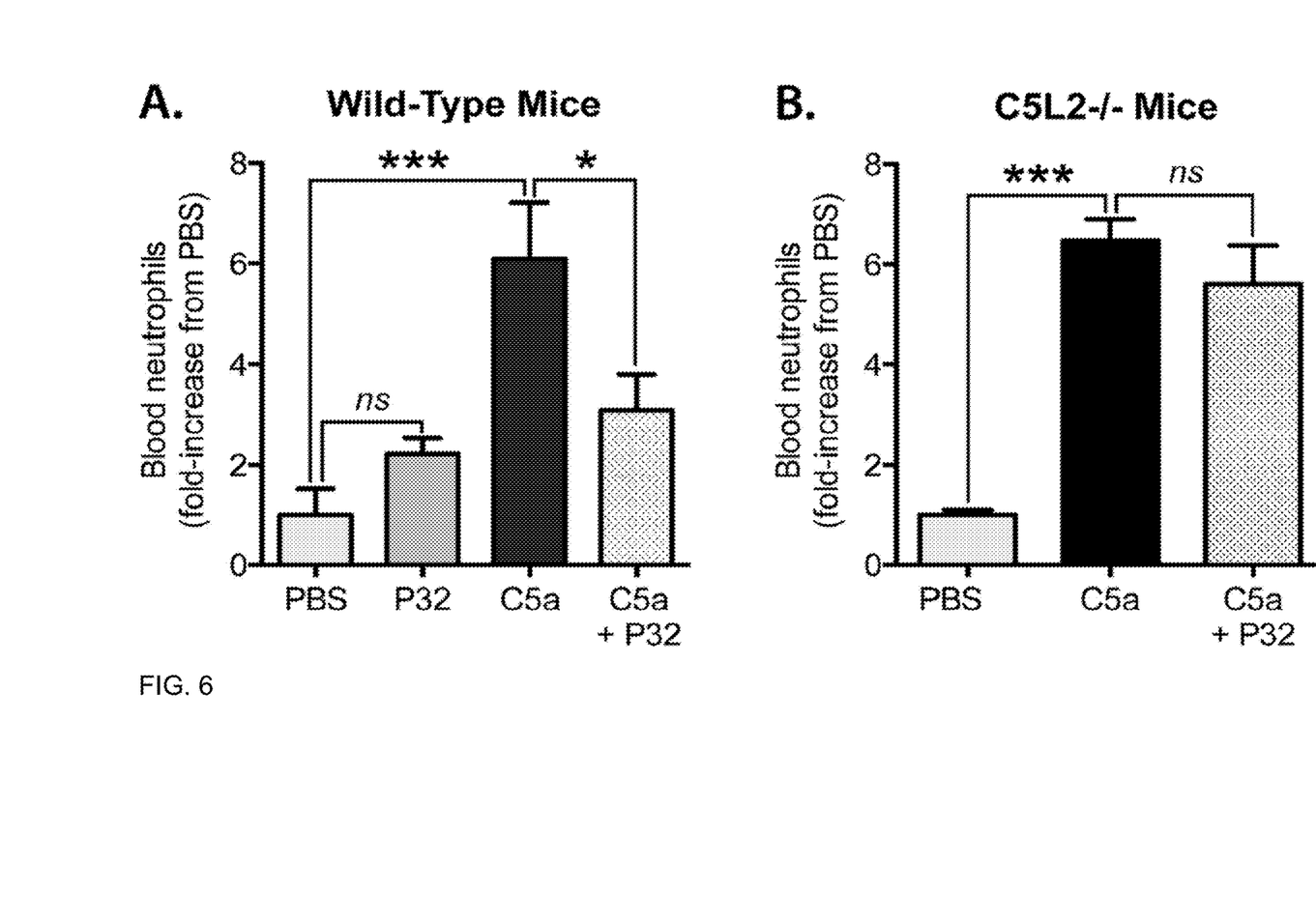
FIG. 6 is a panel of graphs showing that P32 inhibits C5a-induced neutrophil mobilization in vivo in a C5aR2 dependent manner. Neutrophil mobilization quantified 30 min after i.v. injection of PBS, C5a (50 μg/kg), or P32 (3 mg/kg) with and without C5a present into the femoral vein of either C57BL/6J wild-type (6A) or C5aR2$^{-/-}$ (6B) on a C57BL/6J background mice. Total circulating leukocyte counts were determined from blood smears and total white blood cell counts using a hemocytometer. Data are representative from at least 6 mice per treatment group and blood smears in triplicate (n=6). Error bars represent SEM. * P<0.05, *** P<0.001 by one-way ANOVA followed by Dunnett's post hoc test

P32 Inhibits C5a-Induced Neutrophil Mobilization in Wild-type, but not C5aR2−/− Mice To further explore the selectivity of the ligands P32 was tested in a mouse model of C5a-induced neutrophil mobilization (FIG. 6). C5a is known to be one of the most potent induces of neutrophil mobilization and recently C5aR2 has been shown to be required for human mast cell adhesion and migration. When P32 was injected i.v. with C5a it was able to significantly inhibit neutrophil mobilization but when the same experiment was repeated in C5aR2−/− mice this effect of P32 was attenuated. Assuming a mouse blood volume of 2 mL for a 25 g mouse, a concentration of 3 mg/kg would result in Cmax blood concentrations of ~50 uM, a dose within the active range of this compound from our in vitro studies Discussion The inventors have utilised a novel computationally-designed library of 61 hexa-, hepta- and octapeptides[27] based on the C-terminal sequence of C5a (C-terminal octapeptide sequence=HKDMQLGR-OH (SEQ ID NO:3)) to discover the first selective ligands for C5a2 (C5L2/GPR77). Subsequently, it is shown that these ligands can recruit β-arrestin 2 via C5a2, modulate C5a-induced ERK1/2 activation and specifically inhibit IL-6 release from human macrophages. C5a2 was first thought to be solely a recycling decoy receptor, expressed by cells to remove excess C5a from the extracellular fluid, in order to avoid the detrimental C5a1-mediated effects of high C5a concentrations[14]. It has now been shown that C5a2 has additional roles in regulating the release of some cytokines and in a number of inflammatory conditions[15, 20, 32, 34]. One of the major impediments to a better understanding of the role of C5a2 is the dearth of selective ligands[26].

Previously, it has been shown that C5a2 can recruit and form a complex with β-arrestins, which can modulate ERK1/2 signalling in macrophages and neutrophils[13, 17, 35]. The simplistic view of β-arrestins as only regulators of GPCR desensitisation/internalisation has been updated in recent years. β-arrestins are now known to have important signalling roles both independent of and in competition with G-protein signalling in addition to their role in GPCR recycling and chemotaxis[36]. For example, β-arrestin 2 has been shown to act as part of a negative feedback loop that regulates the inflammatory response during sepsis[37]. With the C5a receptors, IL-6 and β-arrestin 2 being shown to be key components in the progression of sepsis[20, 25, 32, 37, 38] the ability to now selectively modulate each of these components should further our understanding of this difficult to treat condition. Sepsis currently accounts for ~350 000 deaths/year with a mortality rate of up to 50% and is responsible for 40% of ICU admissions, costing >$25 billion worldwide annually[39].

The 61-peptide library used in this study was originally designed for binding at C5a1, but the library has recently been shown to contain C3aR-selective agonists with no activity at C5a1[27]. It was then decided to test the library for C5a2 activity due to the similarities between C3aR and the C5a receptors. Using a $^{125}$I-C5a displacement assay on C5a2 expressing membranes the inventors were able to discover two ligands (P32, Ac-RHYPYWR-OH [SEQ ID NO.1], and P59, Ac-LIRLWR-OH [SEQ ID NO.2]) that showed significant displacement of $^{125}$I-C5a. Follow-up testing showed both ligands to have high micromolar affinity for C5aR2 and C5aR1, but more importantly neither displayed any functional activity at C3aR or C5aR1 when previously tested at concentrations up to 100 µM[27]. Having previously established a BRET C5a2 β-arrestin 2 recruitment assay[17] the two hit peptides were tested for the ability to recruit β-arrestin 2 via C5a2. Both, P32 and P59 were able to recruit β-arrestin 2 with ~37- and 6-fold higher efficacy respectively, than the affinity for C5a2. Even though the peptides had significantly higher efficacy for β-arrestin 2 recruitment neither was a full agonist when compared to native C5a.

P32 and P59 both have a C-terminal arginine, which is believed to be a key residue for interaction of C5a with the transmembrane region of C5a2[40]. Both peptides replace the adjacent glycine residue found in C5a with tryptophan and have a hydrophobic residue (Leu or Tyr) at the next position (Leu in C5a), but otherwise differ from C5a. The original library of 61 peptides contained some closely related peptides (differing at one or two positions from P32 and P59) that did not show significant activity in the original radioligand displacement screening assay. In order to begin to establish structure-activity relationships (SAR) the ligand displacement $K_i$ and/or β-arrestin 2 recruitment $EC_{50}$ of these compounds will be determined, along with a set of analogues based on the P32/P59 sequences. Of the two initial hits, P59 shows greater potential for development as it retains similar or better potency as P32 but possesses one less residue and reduced overall charge. There is precedent for converting peptide ligands of complement receptors into potent small-molecules[41], and peptidomimetic approaches will also be investigated.

Here, two selective ligands (P32, P59) for C5a2 have been discovered which are partial agonists (when compared to C5a) for β-arrestin 2 recruitment. The selectivity of these ligands was further evidenced by their inability to recruit β-arrestin 2 via C5a1 or up-regulate heteromer formation between the C5a receptors. These ligands can be used as a medicinal chemistry template for development of higher affinity selective ligands for C5a2. The finding that the C5a2 ligands can inhibit a significant portion of the release of the pro-inflammatory cytokine IL-6, in human macrophages, through β-arrestin 2 signalling, can lead to new methods to modulate IL-6. P32 and P59 were shown to have no direct effect on ERK1/2 activation but could modulate C5a-induced ERK1/2 activation in human macrophages. This result suggests that the ERK1/2 intracellular signalling pathway could be the pathway that β-arrestin 2 modulates following recruitment by C5a2 to inhibit the release of IL-6. The discovery of these C5a2 ligands will now allow complement researchers to selectively probe the functional role of C5a2 in vitro and in vivo, leading to the development of new treatments for a number of inflammatory conditions.

EXAMPLE 2

Methods
Materials

β-arrestin 2-Rluc8 and β-arrestin 2-Venus clones were kindly supplied by Associate Prof. Kevin Pfleger (WAIMR, UWA, Perth, Australia). C5a2 cDNA was supplied by Missouri S&T cDNA Resource Center (www.cdna.org). C5a1-Rluc8 and C5a2-Venus clones were generated previously[31] and kind permission for use of the RLuc8 and Venus constructs was provided by Sanjiv Gambhir (Rluc8, Stanford University, CA, USA) and Atsushi Miyawaki (Venus, RIKEN Brain Science Institute, Wako-city, Japan). Human recombinant C5a was purchased from Sino Biologicals (Beijing, China), human isolated C3a, C3a-des Arg and C5a-des Arg were purchased from Merck Biosciences (Darmstadt, Germany). Glycerol, E. coli-derived LPS, BSA, $MgCl_2$, $CaCl_2$, Tris-HCL, DMSO and HEPES were purchased from Sigma-Aldrich (St Louis, Mo., USA). DMEM, phenol-red free DMEM, IMDM, FBS, streptomycin, penicillin, hygromycin B, trypsin-EDTA and PBS were purchased from Life Technologies (Carlsbad, USA). Recombinant human macrophage-CSF (M-CSF) was purchased from PeproTech (Rocky Hill, N.J., USA).

Design of the Peptide Library

The peptide library consisted of 61 octa-, hepta- and hexapeptides designed around the C-terminal sequence and structure of C5a. A two-stage de novo protein design computational framework was used to construct the peptide library, based on flexible structural templates of C5a from molecular dynamics simulations, as previously described[27]. The full list of sequences of the peptide library is in Halai et al, 2014[27]. The computational framework, its evolution and applications in peptide design are described in[27, 42, 43]

Peptide Synthesis

All peptides were synthesized by GenScript (Piscataway, N.J.) with acetylated N-termini at >95% purity. The C-termini of all peptides was unblocked. Purity was confirmed by analytical HPLC. The 61 peptides of the library were dissolved in dimethyl sulfoxide (DMSO) at a stock concentration of 10 mM and stored at −20° C. till needed for assay. Lead peptides were then dissolved in DMSO at a stock concentration of 100 mM.

Cell Culture and Transfection

HEK293 cells were maintained in DMEM containing 10% FBS, 50 IU $mL^{-1}$ penicillin, 50 mg $mL^{-1}$ streptomycin (Life technologies) at 37° C. and 5% $CO_2$. Flp-In™ CHO cells stably expressing human C5a2 were generated in-house using the Flp-In™ system (Life Technologies). The Flp-In™ CHO-05a2 were cultured in a buffer of Ham's F12, 10% FBS, 50 IU $mL^{-1}$ penicillin, 50 μg $mL^{-1}$ streptomycin and 1000 μg $mL^{-1}$ hygromycin B (Life Technologies). Cells were passaged at 80% confluence using 0.05% trypsin: EDTA in phosphate-buffered saline (PBS), pH 7.4. All cells in culture, once seeded, were incubated at 37° C. with 5% $CO_2$, unless stated otherwise. Transient transfections were performed 24 h after seeding cells at 1×10$^6$ cells per well in a 100-mm dish. X-tremeGENE 9 transfection reagent (Roche, Basel, Switzerland) was used according to the manufacturer's instructions. Cells were collected 24 h after transfection with 0.05% trypsin-EDTA in PBS (Life Technologies). To generate HMDM, human monocytes were isolated from buffy coat blood supplied by unknown donors by the Australian Red Cross Blood Service (Kelvin Grove, Australia) using Ficoll-Plaque Plus (GE Healthcare, Rydalmere, NSW, Australia) and density centrifugation. CD14$^+$ cell selection was performed using MACS magnetic beads (Miltenyi Biotec, Macquarie Park, NSW, Australia)[44]. Isolated CD14$^+$ monocytes were differentiated in culture for 7 days with 10 ng $ml^{-1}$ human M-CSF (Miltenyi Biotec) into HMDM in the presence of IMDM containing L-glutamine supplemented with 10% FBS, 50 IU $ml^{-1}$ penicillin and 50 mg $ml^{-1}$ streptomycin (Life Technologies)[45].

C5a2 Membrane Preparation

Membranes were prepared from Flp-In CHO-05a2 cells by a previously described method[46]. Briefly, cells were washed with PBS, pH 7.4, and harvested into buffer (50 mM Tris-HCl, pH 7.4, 5 mM $MgCl_2$, 1 mM $CaCl_2$) before homogenizing with a Polytron homogenizer for 3 min on setting 22. Cells were centrifuged at 150×g for 5 min at 4° C. The supernatant was recovered and centrifuged at 22 000×g for 1 h at 4° C. Membrane pellets were then resuspended in 0.4 mL of ice-cold buffer (50 mM Tris-HCl, pH 7.4, 5 mM $MgCl_2$, 1 mM $CaCl_2$, containing 10% glycerol) with aliquots stored at −80° C. The protein concentration of the membrane preparation was determined by Bradford method[47].

C5a2 Receptor Binding Studies

C5a2 receptor binding studies were performed using a modification of a previously described scintillation proximity assay (SPA) method[48]. Briefly, C5a2 SPA studies were performed in 96-well white isoplates with clear flat bottoms (Perkin Elmer, Waltham, Mass., USA). SPA beads (200 μg/well) were added, following the addition of various concentrations of competing ligands or buffer (6 pM to 500 μM) in a total volume of 80 μL of assay buffer (50 mM Tris-HCl, pH 7.4, 0.5% BSA, 5 mM $MgCl_2$, 1 mM $CaCl_2$). $^{125}$I-C5a (~20 pM) (specific activity, 2200 Ci $mmol^{-1}$) (Perkin Elmer) was added to C5a2 membrane preparations (~2 μg/well). The final reaction volume per well comprised 20 μL of ligand/buffer, 20 μL of SPA beads, 20 μl of membrane and the assay was initiated by the addition of 20 μL of $^{125}$I-C5a. The plate was then sealed using TopSeal-A (Perkin Elmer) sealing film and incubated with shaking for 1 h at room temperature. Radioligand binding was then assessed for 30 s/well using a 1450 Microbeta scintillation counter (Perkin Elmer).

BRET Assays for Recruitment of β-arrestin 2 to C5a Receptors and between C5a Receptors Assays were performed as a ligand-induced BRET experiment similar to previously described[17, 31, 49]. In brief, HEK293 cells were transiently transfected with either C5a1-Rluc8 and β-arrestin 2-Venus or C5a2-Venus and β-arrestin 2-Rluc8 or C5a1-Rluc8 and C5a2-Venus in a 100-mm dish. 24 h after transfection cells were collected and transferred to a 96-well white microplate (Corning, N.Y., USA) in phenol-red free DMEM containing 5% FBS and 25 mM HEPES (Life Technologies). Cells were allowed to settle for 24 h and then were incubated with 30 µM Enduren (Promega, Madison, Wis., USA) for 2 h at 37° C. and 5% $CO_2$ to ensure that the substrate had reached equilibrium. Following incubation BRET baseline measurements were taken for 15 min then ligands were added to plate and BRET measurements were taken for a further 1 h at 37° C. using a POLARstar optima microplate reader (BMG Labtech, Ortenberg, Germany). Filtered light emissions were sequentially measured for 1 s in each of the following windows 460-490 nm and 520-550 nm, both before and following ligand addition. The ligand-induced BRET ratio was calculated by subtracting the ratio of 520-550 nm emission over the 460-490 nm emission for a vehicle-treated sample from a ligand-treated sample of the same aliquot of cells in triplicate. The BRET ratio was calculated by subtracting the ratio of 520-550 nm emission over the 460-490 nm emission for a cell sample containing the C5a1-Rluc8 or β-arrestin 2-Rluc8 construct from a cell sample containing both the C5a1-Rluc8 and β-arrestin 2-Venus or C5a2-Venus and β-arrestin 2-Rluc8 or C5a1-Rluc8 and C5a2-Venus constructs. Peptides were also tested for ligand-induced β-arrestin 2 recruitment at 100 µM using DiscoveRx PathHunter kits for human C5a1 and C5a2 (DiscoveRx Corporation. Birmingham, UK), according to the manufacturer's instructions.

ERK1/2 Phosphorylation Assay

ERK1/2 phosphorylation assays were performed using the Alphascreen Surefire ERK1/2 kit (Perkin Elmer) as per manufacturers' instructions. Briefly, HMDM were seeded at 50 000 cells/well in 96-well tissue culture plates (Nunc, Waltham, Mass., USA) and serum starved overnight. Ligands were prepared in serum-free media. P32 and P59 were pre-incubated with cells for 30 min at 37° C. and 5% $CO_2$, prior to the addition of C5a (5 nM) for 10 min at 37° C. and 5% $CO_2$. Media was then removed and cells lysed with lysis buffer for 10 min on a shaker, 4 µL of lysate was transferred to a white 384-well proxiplate plate (Perkin Elmer) and incubated in the presence of 7 µL of reaction mix. The plate was sealed with TopSeal-A, incubated for 2 h at 37° C. and measured on an M1000Pro plate reader (Tecan, Mannedorf, Switzerland).

Measurement of Cytokine Release from HMDMs

Briefly, HMDMs were seeded in 96 well tissue culture plates (Nunc) at 100 000 cells/well and allowed to adhere overnight at 37° C. and 5% $CO_2$. The next day HMDMs were stimulated with E. coli derived LPS (10 ng ml$^{-1}$) only or LPS (10 ng ml$^{-1}$) and either C5a or C5a2 ligands at various concentrations (1-100 nM (C5a) or 0.1-100 µM (C5a2 ligands)). For testing cytokine release in the presence of C5a1 antagonist (PMX53), cells were pre-incubated with PMX53 at 10 µM for 30 min prior to addition of C5a or C5a2 ligands. Following ligand addition HMDMs were returned to 37° C. and 5% $CO_2$ incubator and 24 h after stimulation supernatant was removed from cells and transferred to 96 well polypropylene microplate (Nunc) and stored at −20° C. till needed for assay. Quantification of cytokine release was performed using ELISA kits (BD OptEIA™) as per manufacturers' instructions (BD Biosciences, San Jose, Calif., USA).

Data and Statistical Analysis

The Graphpad Prism version 6 software was used for all statistical and graphical analysis (Graphpad Software, La Jolla, Calif., USA). Sigmoidal curves were fitted to the dose-response curves using non-linear regression. Data from at least three separate experiments are expressed as mean, and error bars represent SEM. Statistical analysis was performed using a one-way ANOVA with Dunnett's or Sidak's correction, for multiple comparisons, differences were considered significant if P<0.05.

REFERENCES

The following publications are incorporated by reference herein in their entireties:

1. Klos A, Wende E, Wareham K J, Monk P N. International Union of Pharmacology. LXXXVII. Complement Peptide C5a, C4a, and C3a Receptors. *Pharmacological Reviews* 2013; 65: 500-543.
2. Denny K J, Coulthard L G, Jeanes A, Lisgo S, Simmons D G, Callaway L K et al. C5a receptor signaling prevents folate deficiency-induced neural tube defects in mice. *J Immunol* 2013; 190: 3493-9.
3. Monk P N, Scola A M, Madala P, Fairlie D P. Function, structure and therapeutic potential of complement C5a receptors. *Br J Pharmacol* 2007; 152: 429-448.
4. Manthey H D, Woodruff T M, Taylor S M, Monk P N. Complement component 5a (C5a). *Int J Biochem Cell Biol* 2009; 41: 2114-7.
5. Klos A, Tenner A J, Johswich K-O, Ager R R, Reis E S, Kohl J. The role of the anaphylatoxins in health and disease. *Mol Immunol* 2009; 46: 2753-2766.
6. Woodruff T M, Ager R R, Tenner A J, Noakes P G, Taylor S M. The role of the complement system and the activation fragment C5a in the central nervous system. *Neuromolecular Med* 2010; 12: 179-92.
7. Ward P A. The dark side of C5a in sepsis. *Nature Rev Immunol* 2004; 4: 133-142.
8. Riedemann N C, Guo R-F, Sarma V J, Laudes U, Huber-Lang M, Warner R L et al. Expression and Function of the C5a Receptor in Rat Alveolar Epithelial Cells. *J Immunol* 2002; 168: 1919-1925.
9. Gerard N P, Gerard C. The chemotactic receptor for human C5a anaphylatoxin. *Nature* 1991; 349: 614-617.
10. Cain S A, Monk P N. The Orphan Receptor C5L2 Has High Affinity Binding Sites for Complement Fragments C5a and C5a des-Arg74. *J Biol Chem* 2002; 277: 7165-7169.
11. Okinaga S, Slattery D, Humbles A, Zsengeller Z, Morteau O, Kinrade M B et al. C5L2, a Nonsignaling C5A Binding Protein. *Biochemistry* 2003; 42: 9406-9415.
12. Van Lith L H, Oosterom J, Van Elsas A, Zaman G J. C5a-stimulated recruitment of beta-arrestin2 to the non-signaling 7-transmembrane decoy receptor C5L2. *J Biomol Screen* 2009; 14: 1067-75.
13. Bamberg C E, Mackay C R, Lee H, Zahra D, Jackson J, Lim Y S et al. The C5a Receptor (C5aR) C5L2 Is a Modulator of C5aR-mediated Signal Transduction. *J Biol Chem* 2010; 285: 7633-7644.
14. Scola A M, Johswich K O, Morgan B P, Klos A, Monk P N. The human complement fragment receptor, C5L2, is a recycling decoy receptor. *Mol Immunol* 2009; 46: 1149-62.
15. Chen N-J, Mirtsos C, Suh D, Lu Y-C, Lin W-J, McKerlie C et al. C5L2 is critical for the biological activities of the anaphylatoxins C5a and C3a. *Nature* 2007; 446: 203-207.

16. Gao H, Neff T A, Guo R-F, Speyer C L, Sarma J V, Tomlins S et al. Evidence for a functional role of the second C5a receptor C5L2. *FASEB J* 2005; 19: 1003-1005.

17. Croker D E, Halai R, Kaeslin G, Wende E, Fehlhaber B, Klos A et al. C5a2 can modulate ERK1/2 signaling in macrophages via heteromer formation with C5a1 and beta-arrestin recruitment. *Immunol Cell Biol* 2014; 92: 631-639.

18. Jain U, Woodruff T M, Stadnyk A W. The C5a receptor antagonist PMX205 ameliorates experimentally induced colitis associated with increased IL-4 and IL-10. *Br J Pharmacol* 2013; 168: 488-501.

19. Huber-Lang M, Sarma V J, Lu K T, McGuire S R, Padgaonkar V A, Guo R-F et al. Role of C5a in Multi-organ Failure During Sepsis. *J Immunol* 2001; 166: 1193-1199.

20. Rittirsch D, Flierl M A, Nadeau B A, Day D E, Huber-Lang M, Mackay C R et al. Functional roles for C5a receptors in sepsis. *Nat Med* 2008; 14: 551-557.

21. Ward P A, Guo R F, Riedemann N C. Manipulation of the complement system for benefit in sepsis. *Crit Care Res Pract* 2012; 2012: 427607.

22. Fiocchi C. Inflammatory bowel disease: etiology and pathogenesis. *Gastroenterology* 1998; 115: 182-205.

23. Johswich K, Martin M, Bleich A, Kracht M, Dittrich-Breiholz O, Gessner J E et al. Role of the C5a receptor (C5aR) in acute and chronic dextran sulfate-induced models of inflammatory bowel disease. *Inflamm Bowel Dis* 2009; 15: 1812-23.

24. Allocca M, Jovani M, Fiorino G, Schreiber S, Danese S. Anti-IL-6 Treatment for Inflammatory Bowel Diseases: Next Cytokine, Next Target. *Curr Drug Targets* 2013; 14: 1508-1521.

25. Riedemann N C, Neff T A, Guo R F, Bernacki K D, Laudes I J, Sarma J V et al. Protective effects of IL-6 blockade in sepsis are linked to reduced C5a receptor expression. *J Immunol* 2003; 170: 503-7.

26. Li R, Coulthard L G, Wu M C, Taylor S M, Woodruff T M. C5L2: a controversial receptor of complement anaphylatoxin, C5a. *FASEB J* 2013; 27: 855-64.

27. Halai R, Bellows-Peterson M L, Branchett W, Smadbeck J, Kieslich C A, Croker D E et al. Derivation of ligands for the complement C3a receptor from the C-terminus of C5a. *Eur J Pharmacol* 2014; 745: 176-181.

28. Johswich K, Klos A. C5L2—an anti-inflammatory molecule or a receptor for acylation stimulating protein (C3a-desArg)? *Adv Exp Med Biol* 2007; 598: 159-80.

29. Johswich K, Martin M, Thalmann J, Rheinheimer C, Monk P N, Klos A. Ligand Specificity of the Anaphylatoxin C5L2 Receptor and Its Regulation on Myeloid and Epithelial Cell Lines. *J Biol Chem* 2006; 281: 39088-39095.

30. Kenakin T. Collateral efficacy in drug discovery: taking advantage of the good (allosteric) nature of 7T M receptors. *Trends Pharmacol Sci* 2007; 28: 407-415.

31. Croker D E, Halai R, Fairlie D P, Cooper M A. C5a, but not C5a-des Arg, induces upregulation of heteromer formation between complement C5a receptors C5aR and C5L2. *Immunol Cell Biol* 2013; 91: 625-633.

32. Bosmann M, Haggadone M D, Zetoune F S, Sarma J V, Ward P A. The interaction between C5a and both C5aR and C5L2 receptors is required for production of G-CSF during acute inflammation. *Eur J Immunol* 2013; 43: 1907-13.

33. Seow V, Lim J, Iyer A, Suen J Y, Ariffin J K, Hohenhaus D M et al. Inflammatory responses induced by lipopolysaccharide are amplified in primary human monocytes but suppressed in macrophages by complement protein C5a. *J Immunol* 2013; 191: 4308-16.

34. Wang R, Lu B, Gerard C, Gerard N P. Disruption of the complement anaphylatoxin receptor C5L2 exacerbates inflammation in allergic contact dermatitis. *J Immunol* 2013; 191: 4001-9.

35. Hsu W C, Yang F C, Lin C H, Hsieh S L, Chen N J. C5L2 is required for C5a-triggered receptor internalization and ERK signaling. *Cell Signal* 2014; 26: 1409-19.

36. Defea K. Beta-arrestins and heterotrimeric G-proteins: collaborators and competitors in signal transduction. *Br J Pharmacol* 2008; 153 Suppl 1: S298-309.

37. Fan H, Bitto A, Zingarelli B, Luttrell L M, Borg K, Halushka P V et al. Beta-arrestin 2 negatively regulates sepsis-induced inflammation. *Immunology* 2010; 130: 344-51.

38. Riedemann N C, Guo R-F, Hollmann T J, Gao H, Neff T A, Reuben J S et al. Regulatory role of C5a in LPS-induced IL-6 production by neutrophils during sepsis. *FASEB J* 2004; 18: 370-2.

39. Schorr C A, Dellinger R P. The Surviving Sepsis Campaign: past, present and future. *Trends Mol Med* 2014; 20: 192-4.

40. Scola A M, Higginbottom A, Partridge L J, Reid R C, Woodruff T, Taylor S M et al. The role of the N-terminal domain of the complement fragment receptor C5L2 in ligand binding. *J Biol Chem* 2007; 282: 3664-71.

41. Reid R C, Yau M K, Singh R, Hamidon J K, Reed A N, Chu P et al. Downsizing a human inflammatory protein to a small molecule with equal potency and functionality. *Nature Commun* 2013; 4: 2802.

42. Bellows-Peterson M L, Fung H K, Floudas C A, Kieslich C A, Zhang L, Morikis D et al. De novo peptide design with C3a receptor agonist and antagonist activities: theoretical predictions and experimental validation. *J Med Chem* 2012; 55: 4159-68.

43. Klepeis J L, Floudas C A, Morikis D, Tsokos C G, Argyropoulos E, Spruce L et al. Integrated computational and experimental approach for lead optimization and design of compstatin variants with improved activity. *J Am Chem Soc* 2003; 125: 8422-3.

44. Verreck FAW. Human IL-23-producing type 1 macrophages promote but IL-10-producing type 2 macrophages subvert immunity to (myco)bacteria. *Proc Natl Acad Sci USA* 2004; 101: 4560-4565.

45. Halili M A, Andrews M R, Labzin L I, Schroder K, Matthias G, Cao C et al. Differential effects of selective HDAC inhibitors on macrophage inflammatory responses to the Toll-like receptor 4 agonist LPS. *J Leukoc Biol* 2010; 87: 1103-14.

46. Halai R, Croker D E, Suen J Y, Fairlie D P, Cooper M A. A Comparative Study of Impedance versus Optical Label-Free Systems Relative to Labelled Assays in a Predominantly Gi Coupled GPCR (C5aR) Signalling. *Biosensors* 2012; 2: 273-290.

47. Bradford M M. A rapid and sensitive method for the quantitation of microgram quantities of protein utilizing the principle of protein-dye binding. *Anal Biochem* 1976; 72: 248-54.

48. Dutertre S, Croker D, Daly N L, Andersson A, Muttenthaler M, Lumsden N G et al. Conopressin-T from Conus tulipa reveals an antagonist switch in vasopressin-like peptides. *J Biol Chem* 2008; 283: 7100-8.
49. Kocan M, Dalrymple M B, Seeber R M, Feldman B J, Pfleger K D. Enhanced BRET Technology for the Monitoring of Agonist-Induced and Agonist-Independent Interactions between GPCRs and beta-Arrestins. *Front Endocrinol* (Lausanne) 2010; 1: 12.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the invention and the following claims.

What is claimed is:

1. A pharmaceutical composition comprising a C5a receptor 2 (C5aR2) ligand that selectively modulates C5aR2 compared to C5a receptor 1 (C5aR1) in a pharmaceutically acceptable formulation selected from the group consisting of a tablet, suppository, pill, capsule, powder, suspension, ointment, lotion, or liquid other than just water.

2. The C5aR2 ligand of claim 1, wherein the ligand is a polypeptide or peptide comprising SEQ ID NO:1 or is a peptide of 100 amino acids or less comprising SEQ ID NO:2.

3. The C5aR2 ligand of claim 1, wherein the ligand is a peptide of 100 amino acids or less comprising SEQ ID NO:1 or SEQ ID NO:2, or an analog, sequence variant, or peptidomimetic of the peptide.

4. The C5aR2 ligand of claim 1, wherein the ligand is a polypeptide or peptide comprising amino acid sequence TyrTtpArg of SEQ ID NO:1 or is a peptide of 100 amino acids or less comprising LeuTrpArg of SEQ ID NO:2.

5. A C5aR2 ligand that selectively modulates C5aR2 compared to C5aR1, wherein the ligand is a polypeptide or peptide of 100 amino acids or less comprising an N-terminally modified SEQ ID NO:1 or N-terminally modified SEQ ID NO:2.

6. The C5aR2 ligand of claim 5 wherein the N-terminally modified SEQ ID NO:1 or N-terminally modified SEQ ID NO:2 are each N-terminally acetylated.

7. A C5aR2 ligand that selectively modulates C5aR2 compared to C5aR1, wherein the ligand is an N-terminally modified peptide of 100 amino acids or less comprising SEQ ID NO:1 or SEQ ID NO:2, or an analog, sequence variant, or peptidomimetic of the peptide.

8. The C5aR2 ligand of claim 7 wherein the N-terminally modified peptide is N-terminally acetylated.

9. A pharmaceutical composition comprising a C5a receptor 2 (C5aR2) ligand that selectively modulates C5aR2 compared to C5a receptor 1 (C5aR1), where the ligand is an N-terminally modified polypeptide or an N-terminally modified peptide.

10. The C5aR2 ligand of claim 9 wherein the N-terminally modified polypeptide and peptide are each N-terminally acetylated.

11. An N-terminally acetylated peptide comprising Tyr-TrpArg of SEQ ID NO:1 or an N-terminally acetylated peptide of 100 amino acids or less comprising LeuTrpArg of SEQ ID NO:2.

12. The C5aR2 ligand of claim 11 wherein the N-terminally modified peptide is N-terminally acetylated.

* * * * *